United States Patent [19]
Lok et al.

[11] Patent Number: 6,017,445
[45] Date of Patent: Jan. 25, 2000

[54] MEASUREMENT OF THE CATION CONDUCTIVITY OF WATER

[75] Inventors: Gerrit Willem Lok, Alberton; Sean Peters; Gregory Allan Olivier, both of Johannesburg, all of South Africa

[73] Assignee: Eskom, Sandton, South Africa

[21] Appl. No.: 09/076,588

[22] Filed: May 12, 1998

Related U.S. Application Data

[60] Provisional application No. 60/046,401, May 13, 1997, and provisional application No. 60/075,677, Feb. 24, 1998.

[30] Foreign Application Priority Data

Aug. 22, 1997 [ZA] South Africa .......................... 97/7537

[51] Int. Cl.$^7$ .............................. B01D 17/06; C25B 9/00
[52] U.S. Cl. ...................... 210/85; 243/257.2; 243/263; 204/257
[58] Field of Search ..................................... 204/257, 263; 205/746, 748, 770; 210/638, 748, 85, 263, 257.2, 243, 294, 321.6

[56] References Cited

U.S. PATENT DOCUMENTS

| | | | |
|---|---|---|---|
| 4,589,968 | 5/1986 | Toomey | 204/257 |
| 4,643,818 | 2/1987 | Seko | 204/257 |
| 4,720,331 | 1/1988 | Billings | 204/257 |
| 4,734,181 | 3/1988 | Cipriano | 204/257 |
| 4,767,519 | 8/1988 | de Nora | 204/257 |
| 4,830,721 | 5/1989 | Bianchi | 204/257 |

OTHER PUBLICATIONS

Proceedings of an International Congress on Membranes and Membrane Processes, held from 18–23, Aug. 1996, Pacifico Yokohama, Conference Center, Yokohama, Japan, Lok, et al. pp. 542 and 543. Plus Nine Unnumbered Pages.

Conlin et al., "Operating Experience of an Electrochemical Cell to aid in the Removal of Cations Prior to Cation Conductivity Determinations in the Power Industry", presented at the Fifth International Congress on Cycle chemistry held from Jun. 10–12, 1997, Charlotte, North Carolina, p. 22, Plus 10 Unnumbered Pages.

Peters, et al., "Operating Experience of an Electrochmeical Cell to Aid in the Removal of Cations Prior to Cation Conductivity Determinations in the Power Industry", Proceedings of the 9$^{th}$ Annual Meeting of the North American Membrane Society held from May 31 to Jun. 4, 1997, in Baltimore, Maryland, p. 4, Plus 18 Unnumbered Pages.

Lok, et al., "Operating Experience of an Electrochemical Cell to aid in the Removal of Cations Prior to Cation Conductivity Determinations in the Power Industry", held from Oct. 21–24, 1997, South Africa, Proceedings of the Second WISA–MTD Workshop. 35 Unnumbered Pages.

*Primary Examiner*—Ernest G. Therkorn
*Attorney, Agent, or Firm*—Frommer Lawrence & Haug LLP; William S. Frommer

[57] ABSTRACT

A method of treating water comprises pausing sample water through an anode compartment of an electrochemical cell, or of an electrochemical cell stage. The anode compartment is separated from a cathode compartment by a water-impermeable membrane capable of transferring positively charged ions or cations only. At the same time, a direct electric current is applied between electrodes in the anode and cathode compartments, and a demineralized water stream is passed through the cathode compartment. Cations of dissolved salts in the sample water pass or migrate across the membrane. Water also dissociates in the anode compartment to generate hydrogen ions, and these hydrogen ions associate with the anions of the dissolved salts, to form the corresponding acids of the dissolved salts.

5 Claims, 7 Drawing Sheets

MEASUREMENT OF THE CATION CONDUCTIVITY OF WATER

This application claims the benefit of U.S. Provisional Application No. 60/046,401, filed May 13, 1997 and U.S. Provisional Application No. 60/075,677, filed Feb. 24, 1998.

FIELD OF THE INVENTION

THIS INVENTION relates to the measurement of the cation conductivity of water. It relates in particular to a method of measuring the conductivity of water; to a method of treating water, particularly water whose cation conductivity is to be measured; to apparatus for treating water, thereby to assist in subsequent measurement of its cation conductivity, and to a water cation conductivity measurement installation.

BACKGROUND OF THE INVENTION

Conductivity (resistivity) measurements are reliable overall indicators of water purity, and the accuracy of such measurements has improved significantly over the past few years. Conductivity measurements are, for example, used for the detection of impurities in steam/water circuits at power plants. The cation conductivity ('CC') of a solution refers to the conductivity of that solution after it has been treated, e.g. has passed through a strong acid cation exchange resin, so that its cations have been replaced or exchanged by hydrogen ions ($H^+$). Cation conductivity is also known as the acid conductivity or KHI value. Since the hydrogen ion has the highest specific ionic conductance of all ionic species, cation conductivity values are capable of improving the sensitivity of measurements for the detection of impurities in water, such as in steam/water circuits. For this reason, cation conductivity values are an effective method for detecting condenser tube leaks in water cooled condenser systems at power plants. The cation conductivity of a solution also gives a good indication of the concentration of anions present in the solution.

A reliable method for the detection of water cation conductivity values already exists. The method involves passing a sample of the solution through a strong acid cation exchange resin column. Any cations present in the sample solution and emanating from dissolved salts are exchanged for hydrogen ions, thereby forming acids corresponding to the dissolved salts. In other words, cations present in the sample solution salt are taken up on the resin while hydrogen ions on the resin are released into the water to associate with the anions originally associated with the cations, thus forming acids corresponding to the dissolved salts. The sample is then passed through a conductivity detection—or measuring cell, which consists of electrodes of specific area and surface condition, spaced a defined distance apart by a controlled cross-section of the process sample. The acid is usually more conductive than the salt, thereby producing an exaggerated conductivity measurement. The disadvantage of this method, however, is that the cation exchange resin is rapidly exhausted, particularly in cases where the steam/water circuit from which the water sample is taken is operated in a high all volatile treatment ('AVT') regime.

OBJECT OF THE INVENTION

It is an object of the invention to provide an improved method of measuring the cation conductivity of water, and an improved method of treating water whose cation conductivity is to be measured.

BROAD DESCRIPTION OF THE INVENTION

According to a first aspect of the invention, there is provided a method of treating water, which comprises parsing sample water through an anode compartment of an electrochemical cell, or of an electrochemical cell stage, in which the anode compartment is separated from a cathode compartment by a water-impermeable membrane capable of transferring positively charged ions or cations only, while applying a direct electric current between electrodes in the anode and cathode compartments and while passing a demineralized water stream through the cathode compartment, thereby to cause cations of dissolved salts in the sample water to pass or migrate across the membrane, with water also dissociating in the anode compartment to generate hydrogen ions and with these hydrogen ions associating with the anions of the dissolved salts, to form the corresponding acids of the dissolved salts.

The method may include passing the sample water from said anode compartment ('the first anode compartment') in said electrochemical cell stage ('the first cell stage') through a second anode compartment in a second electrochemical cell stage ('the second cell stage') provided in a common housing with the first cell stage, while passing the demineralized water stream from said cathode compartment ('the first cathode compartment') through a second cathode compartment of the second cell stage. The sample water stream and the demineralized water stream thus both first pass through the first anode and cathode compartments respectively, and then through the second anode and cathode compartments respectively, ie they flow cocurrently with respect to each other. The compartments may be arranged back-to-back with the two cathode compartments being served by a single or common negative electrode or cathode, while the two anode compartments are each served by a positive electrode or anode. Instead, the compartments may be arranged back-to-back with the two anode compartments being served by a single or common anode, while the two cathode compartments are each served by a separate cathode.

The sample water may, in particular, be ultra pure or chemically treated water, such as boiler feed water, as hereinafter described.

Instead, if desired, the demineralized water stream can pass through the second cathode compartment first, and then through the first cathode compartment, while the sample water passes sequentially through the first and second anode compartments as hereinbefore described, ie the water streams flow counter-currently with respect to each other.

The first and second cell stages are preferably provided in a common or single zone or compartment of the common housing.

The method may include, if desired, e.g. if enhanced cation removal is required, passing the sample water and the demineralized water streams sequentially through a further anode compartment and cathode compartment respectively of at least one further electrochemical cell stage, which is then preferably contained in the same housing as the first and second electrochemical cell stages.

One of these further compartments may then be arranged back-to-back with the second anode compartment or the second cathode compartment with a common electrode serving the back-to-back compartments in similar fashion to that hereinbefore described.

According to a second aspect of the invention, there is provided a method of measuring the cation conductivity of water, which comprises passing sample water whose cation conductivity is to be measured through an anode compartment of an electrochemical cell, or of an electrochemical cell stage, in which the anode compartment is separated from a cathode compartment by a water-impermeable membrane capable of transferring positively charged ions or cations only, while applying a direct electric current between electrodes in the anode and cathode compartments and while passing a demineralized water stream through the cathode compartment, thereby to cause cations of dissolved salts in the water to pass or migrate across the membrane, with water also dissociating in the anode compartment to generate hydrogen ions and with these hydrogen ions associating with the anions of the dissolved salts, to form the corresponding acids of the dissolved salts; and passing the sample water through a conductivity-measuring cell in which the cation conductivity of the water is measured.

The method may include passing the sample water through a strong acid cation exchange resin column in which further dissolved salt cations are exchanged for hydrogen ions present on the resin, thereby also forming the corresponding acids of the dissolved salts, prior to passing the sample water through the conductivity measuring cell.

According to a third aspect of the invention, there is provided a method of measuring the cation conductivity of water, which comprises passing sample water whose cation conductivity is to be measured sequentially through a first anode compartment of a first electrochemical cell stage in which the first anode compartment is separated from a first cathode compartment by a water-impermeable membrane capable of transferring positively charged ions or cations only, while applying a direct electric current between electrodes in the first anode and cathode compartments and then through a second anode compartment of a second electrochemical cell stage in a common housing with the first cell stage, with the second anode compartment similarly separated from a second cathode compartment by a water-impermeable membrane capable of transferring cations only, while applying a direct electric current between electrodes in the second anode and cathode compartments, and while passing a demineralized water stream sequentially through the cathode compartments, thereby to cause cations of dissolved salts in the water to pass or migrate across the membrane, with water also dissociating in the anode compartment to generate hydrogen ions and with these hydrogen ions associating with the anions of the dissolved salts, to form the corresponding acids of the dissolved salts;

optionally, thereafter passing the sample water through a strong acid cation exchange resin column in which further dissolved salt cations are exchanged for hydrogen ions present on the resin, thereby also forming the corresponding acids of the dissolved salts; and passing the sample water through a conductivity-measuring cell in which the cation conductivity of the water is measured.

As hereinbefore described, the first and second electrochemical cell stages may be provided in a common or single zone or compartment of the common housing, and the demineralized water stream may pass through the first cathode compartment to the second cathode compartment so that it flows cocurrently with the sample water.

As also hereinbefore described, either the anode compartments or the cathode compartments may be arranged back-to-back with a common electrode serving them.

As also hereinbefore described, the method may include passing the sample stream and the demineralized water stream sequentially through the anode and cathode compartments respectively of at least one further electrochemical cell stage.

Thus, if a desired degree of treatment is imparted to the sample water in the electrochemical cell stages, the strong acid cation exchange resin column can be dispensed with.

The term "demineralised water" is intended to include water which has been subjected to cation exchange. Thus, sample water exiting the conductivity-measuring cell may be recycled to the cathode compartment(s) of the electrochemical cell stage(s) as demineralized water.

In the electrochemical cell stage(s), cations such as ammonium ions ($NH_4^+$) which are present in the sample water permeate through the membrane, towards the negative electrode or cathode in the cathode compartment. However, anions are attracted towards the anode, while the membrane also repels anions, so that anions present in the same water remain in the anode compartment. In this fashion, effective removal of cations from the sample water is achieved.

Additionally, the following reactions occur during operation of the electrochemical cell stage(s)

A water dissociation reaction (electrolysis) involving the gain of electrons (reduction) occurs at the cathode:

$$2H_2O(aq)+2e^- \rightarrow 2(OH^-)(aq)+H_2(g)\uparrow \quad (1)$$

A water dissociation reaction (electrolysis) involving the loss of electrons (oxidation) occurs at the anode:

$$2H_2O(aq) \rightarrow 4H^+(aq)+O_2(g)\uparrow +4e^- \quad (2)$$

Any hydroxide ions associated with said ammonium ions, and such other anions as are associated with other cations present in the feedstream, will combine with the hydrogen ions produced by the water dissociation reaction in the anode compartment, according to the following reaction schemes:

$$H^+(aq)+OH^-(aq) \leftrightharpoons H_2O(aq) \quad (3)$$

$$nH^+(aq)+AN^{n-}(aq) \leftrightharpoons (H)_n AN(aq) \quad (4)$$

where:

$AN^{n-}$ is other anions of varying negative charge and n is stoichiometric number of moles of hydrogen ions reacting with the anions.

In a similar fashion, the cations which are transferred across the membrane will recombine with the hydroxide ions produced by the water dissociation reaction in the cathode compartment.

$$NH_4^+(aq)+OH^-(aq) \leftrightharpoons NH_4OH(aq) \quad (5)$$

$$M^{n+}(aq)+nOH^-(aq) \leftrightharpoons M(OH)_n(aq) \quad (6)$$

where:

$M^{n+}$ is other cations of varying positive charge and n is stoichiometric number of moles of hydroxide ions reacting with the cations.

The method may include, if desired, pretreating the sample water before passing it through the electrochemical cell or the cell stages. Such pretreatment may comprise passing the sample water through a filter, e.g. a cartridge filter, to remove suspended solids, which may foul the membrane, from the sample water.

The method may include passing the sample water sequentially through a plurality, e.g. two, of the electrochemical cells, before, optionally, passing it through the strong acid cation exchange resin column, and into the conductivity measuring cell.

According to a fourth aspect of the invention, there is provided apparatus for treating water, which apparatus comprises a housing defining at least one electrochemical cell having an anode compartment and a cathode compartment, with a sample water inlet leading into the anode compartment and a sample water outlet leading from the anode compartment, and with a demineralized water inlet leading into the cathode compartment and a demineralized water outlet leading from the cathode compartment;

an electrode in each of the compartments; and a water impermeable membrane capable of transferring cations only, separating the anode compartment from the cathode compartment.

The inlets and outlets may be arranged such that the direction of flow in the compartments is in cocurrent fashion.

The housing may define two of the electrochemical cells, each having the electrodes and the water impermeable membrane. The sample water outlet of a first of the cells may be connected to the sample water inlet of a second of the cells.

According to a fifth aspect of the invention, there is provided a water conductivity measurement installation, which comprises apparatus, according to the fourth aspect of the invention, for treating water, whose conductivity is to be measured;

optionally, a strong cation exchange resin column operatively connected to the sample water outlet of the apparatus; and a conductivity-measuring cell operatively connected to the apparatus or to the column so that sample water can pass from the apparatus or the column to the cell.

According to a sixth aspect of the invention, there is provided apparatus for treating water, which apparatus comprises a housing;

a first electrochemical cell stage in the housing, the first cell stage having a first anode compartment and a first cathode compartment with a first sample water inlet leading into the first anode compartment and a first sample water outlet leading from the first anode compartment and with a first demineralized water inlet/outlet leading into/from the first cathode compartment and a second demineralized water inlet/outlet leading into/from the first cathode compartment;

a second electrochemical cell stage in the housing, the second cell stage having a second anode compartment and a second cathode compartment with a second sample water inlet leading into the second anode compartment and being connected to the first sample water outlet of the first cell stage and a second sample water outlet leading from the second cathode compartment, with a third demineralized water inlet/outlet leading into/from the second cathode compartment and being connected to the second demineralized water inlet/outlet of the first cell stage, and a fourth demineralized water inlet/outlet leading into/from the second cathode compartment;

an electrode associated with each of the compartments; and a water impermeable membrane capable of transferring only cations, for each of the cell stages, the membrane in each cell stage separating its anode compartment from its cathode compartment.

The cell stages may be such that either the first and second anode compartments or the first and second cathode compartments are arranged back-to-back, with a common electrode provided for the back-to-back compartments while a separate electrode is provided in each of the other, ie the non-back-to-back, compartments. Thus, for example, the cathode compartments may be arranged back-to-back with a common negative electrode or cathode, while a separate positive electrode or anode is provided in each of the anode compartments.

As hereinbefore described, the inlets and outlets may be arranged such that the direction of flow of the sample water and demineralized water through the compartments, in use, is in cocurrent fashion.

The apparatus may include at least one further electrochemical cell in the same housing, the further cell also having an anode compartment, a cathode compartment, water inlets and outlets, at least one electrode, and a water impermeable membrane, as hereinbefore described, with the further cell arranged such that sample water and demineralized water can flow sequentially from the first or second cell through the further cell.

According to a seventh aspect of the invention, there is provided a water cation conductivity measurement installation, which comprises apparatus according to the sixth aspect of the invention, for treating water whose cation conductivity is to be measured;

optionally, a strong acid cation exchange resin column operatively connected to the sample water outlet of the apparatus; and a conductivity-measuring cell operatively connected to the apparatus or to the column so that sample water can pass from the apparatus or the column to the cell.

The invention will now be described by way of example with reference to the accompanying diagrammatic drawings.

DETAILED DESCRIPTION OF THE DRAWINGS

In FIGS. 1 to 6, reference numeral 10 generally indicates a water cation conductivity measurement installation, according to the invention.

Figure 1:
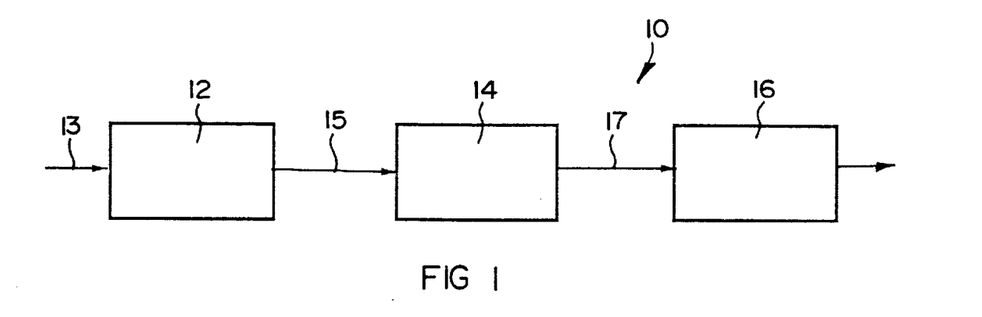
FIG. 1 shows a simplified block diagram of a water cation conductivity measurement installation, according to the invention.

The installation 10 includes apparatus 12 for pretreating sample water, e.g. water from a steam/water circuit of a power station, entering it along a flow line 13.

The apparatus 12 is operatively connected to a strong acid cation exchange resin column 14 by means of a flow line 15. The column 14 in turn is operatively connected to a conductivity measuring cell 16 by means of a flow line 17.

Figure 2:
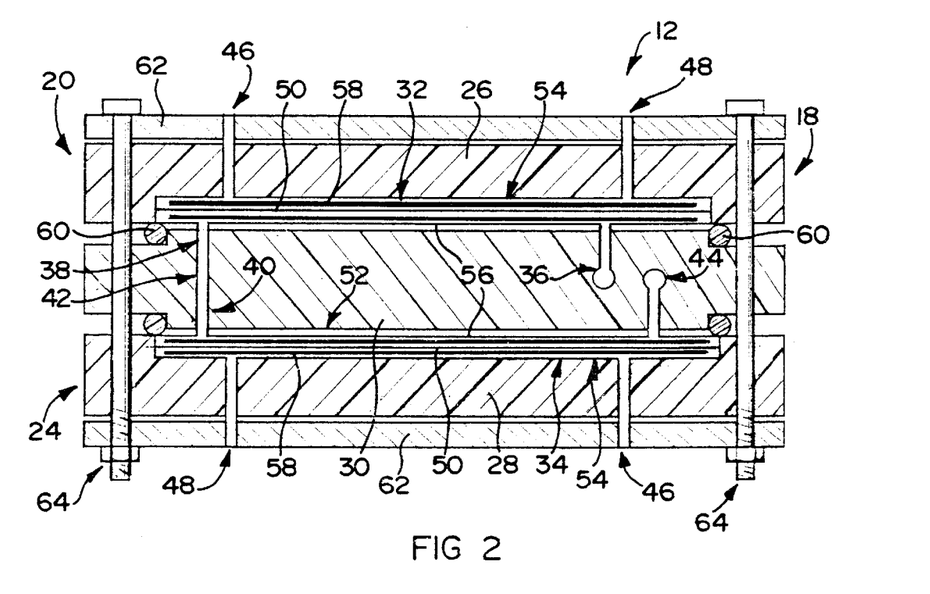
FIG. 2 shows a sectional view of the apparatus 12 shown in FIG. 1.

The apparatus 12 comprises a housing 18 defining a first electrochemical cell 20 as well as a second electrochemical cell 24. The housing 18 comprises outer polypropylene casings 26, 28 and an inner or central polypropylene casing 30. A cell cavity or recess 32 is provided in the outer casing 26, while a cell cavity or recess 34 is provided in the outer casing 28. Polypropylene is used since it is flexible as well as chemically inert.

A sample water inlet 36 to the cavity 32 is provided in the central casing 30, while a sample water outlet 38 from the cavity 32 is also provided in the central casing 30. The outlet 38 is connected to an inlet 40 to the cavity 34 by means of a passageway 42 in the central casing 30. A sample water outlet 44 from the cavity 34 is provided in the central casing 30.

A demineralized water inlet 48 into and an outlet 46 from each of the cavities 32, 34 is provided in each of the outer casings 26, 28.

In each of the cavities 32, 34 is provided a water impermeable membrane 50 capable of permitting passage of cations only. In each case the membrane 50 separates the cavity into an anode compartment 52 and a cathode compartment 54. A platinum plated nickel or a stainless steel anode 56 is provided in each anode compartment 52, while a platinum plated nickel or a stainless steel cathode 58 is provided in each cathode compartment 54.

Rubber O-rings 60 are provided between the inner and outer casings to seal against air and water leakage, and to assist in preventing electrical short circuiting. The casings are held in position by stainless steel supports 62 and stainless steel bolt, washer and nut assemblies 64.

The inlets and outlets are thus arranged so that, in use, sample water passes sequentially from the first cell 20 to the second cell 24, while flow of sample water and demineralized water through the stages is in cocurrent fashion.

The cavities 32, 34 are such that a turbulent, tortuous sample water flow path is provided in each anode compartment 52. For this, polypropylene spacers (not shown) are used. Turbulent sample water flow allows a higher electric current flow per unit area, and aids in keeping the sample water intimately mixed which promotes transfer of ions to the surface of the membrane.

The membrane may be that available in South Africa under the trade name IONICS from Ionics Inc. Thus, the membrane has negative charges affixed to sites throughout the membrane. These fixed negative charges repel negatively charged ions or anions while allowing cations to permeate through it.

The column 14 may be that available in South Africa under the trade name KHI COLUMN from Aquaplan CC, while the cell 16 can be a single conductivity/resistivity transmitter such as model Polymetron Monec C 8920, manufactured by Zellweger Uster AG of Switzerland, and available in South Africa from Krohne (Pty) Limited of Midrand, Gauteng Province.

Figure 3:
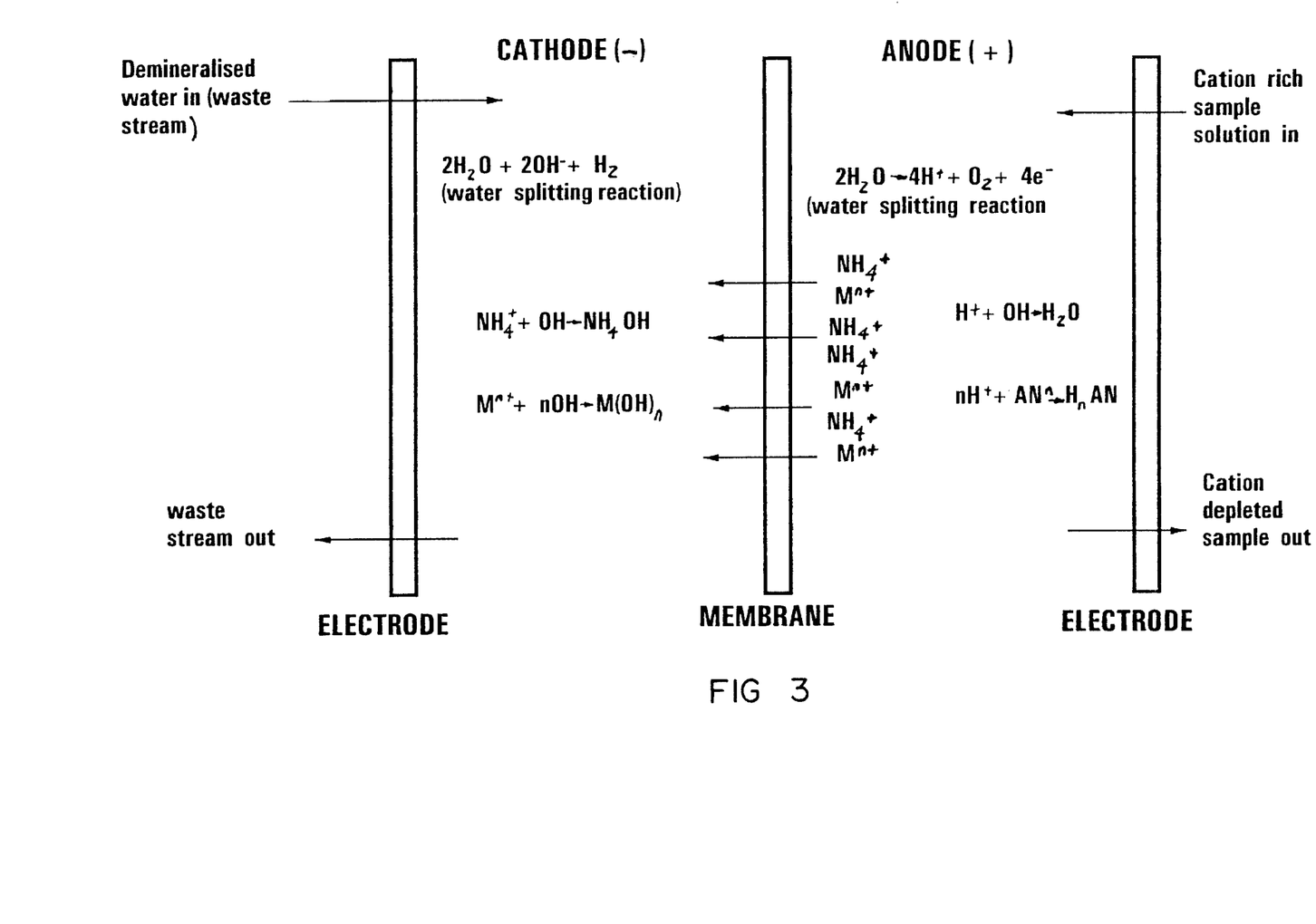
FIG. 3 shows, schematically, the operation of the apparatus of FIG. 2.

In use, sample water from a steam/water circuit of a power station and containing $NH_4OH$ enters the apparatus 12 and passes sequentially through the anode compartments 52 thereof, while demineralized water passes through the cathode compartments 54 in cocurrent fashion. A DC current is passed between the anode 56 and cathode 58 of each cell 20, 24. Reactions (1) to (6) as hereinbefore set out and as indicated in FIG. 3 take place, thereby removing cations of inorganic salts from the sample water, and replacing them by hydrogen to produce acids of the inorganic salts, as hereinbefore described. This will remove most of the salt cations present in the sample water, while secondary scrubbing of any remaining salt cations will be effected by means of cation exchange in the column 14, before cation conductivity measurement is effected in the cell 16.

TEST 1

Comparative simulated condenser tube leak tests were performed on $NH^+_4$-buffered condensate water, as employed by steam operated turbo generators, in the one case using an installation in accordance with the invention and as depicted in FIG. 1, and in the other case using a resin column only to treat the water, ie not using the apparatus 12.

Figure 4:
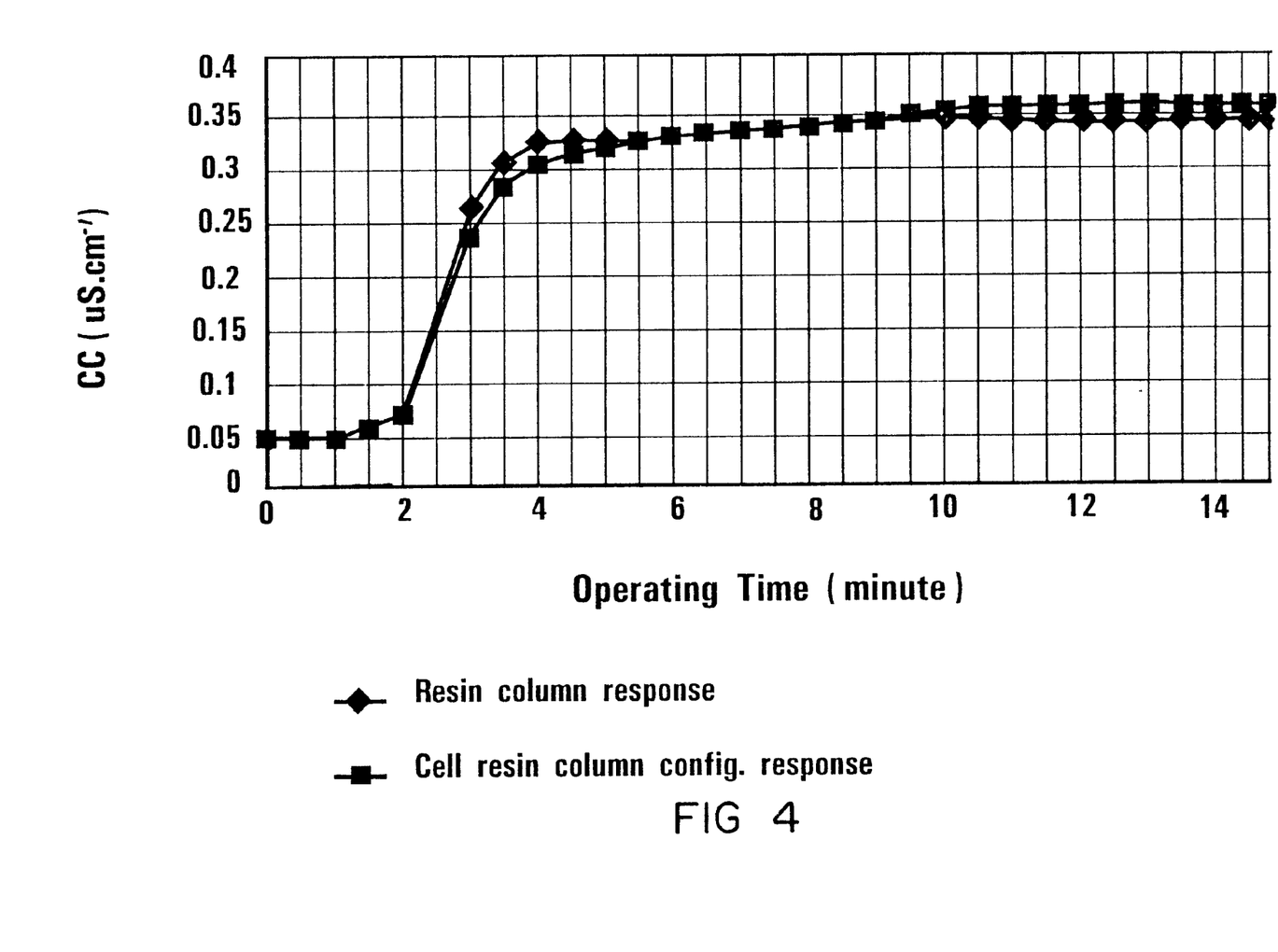
FIGS. 4, 5 and 6 show conductivity measurement graphs for comparative tests which were conducted.

The results of these comparative tests are shown in FIG. 4, from which it can be seen that the responses in the two cases were almost identical.

TEST 2

In this test, similar comparative tests were done on a condensate from a plant operating at elevated levels of AVT ('all volatile treatment'), with the condensate being obtained from the condensate extraction pump ('CEP'). The sample had a specific conductivity value of 12,0-14,0 uS.cm$^{-1}$ at 25° C. ($K_{25}$).

Figure 5:
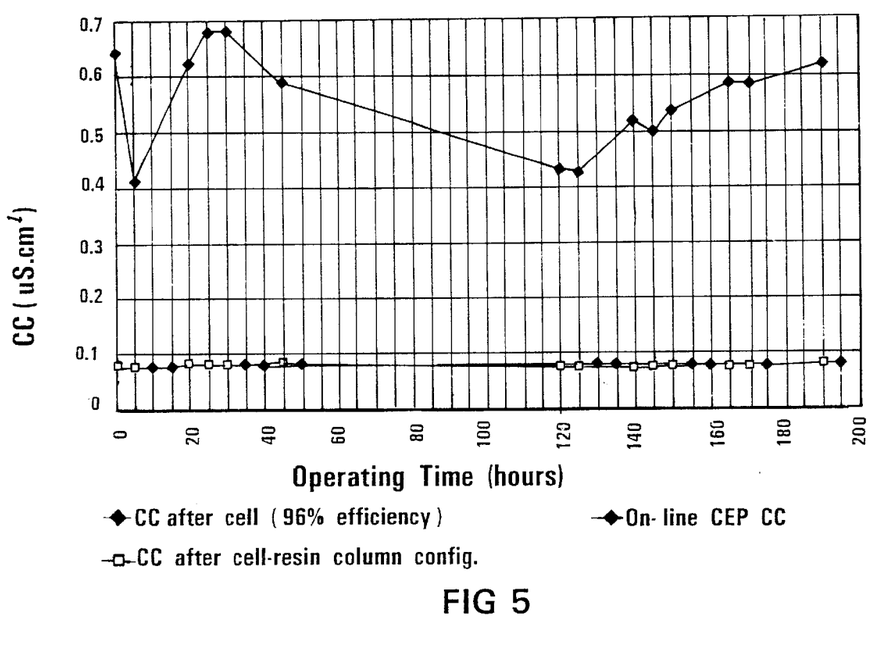

The results can be seen in FIG. 5 which reflects cation conductivity ('CC') vs operating time in the case where the installation was used, first, without the apparatus 12, i.e. 'on-line CEP CC', secondly, with the apparatus 12, measurements being taken between the apparatus 12 and the cation exchange resin column 14 ('CC after cell'), and, thirdly, with the apparatus 12, measurements being taken after the cation exchange resin column 14 ('CC after the cell—resin column configuration').

It was found that the operating life of the resin column was extended by 3000%, and that 96% of cations were removed by the apparatus 12, based on the cation conductivity of the condensate.

TEST 3

Figure 6:
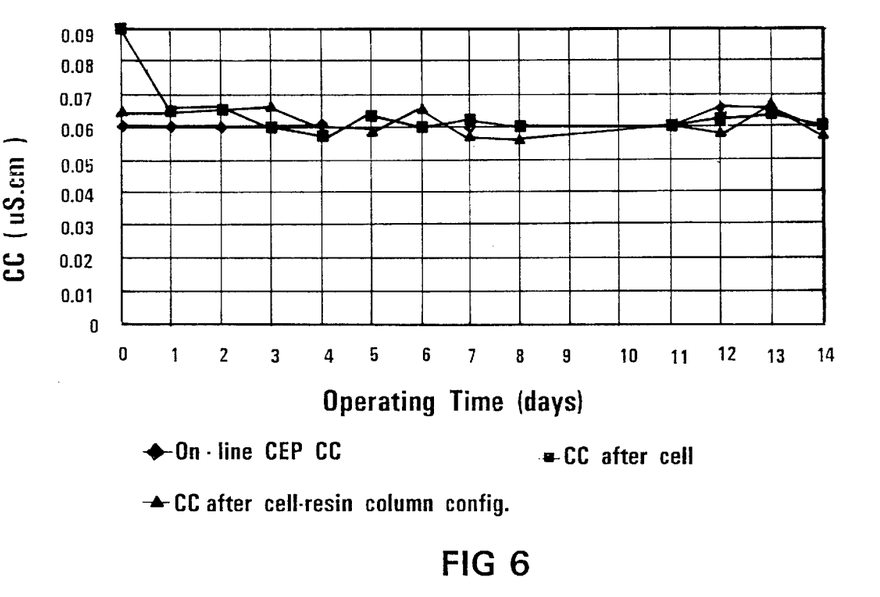

The sample water used was similar to that of Test 2, except that it had a $K_{25}$ value of 3–5 uS.cm$^{-1}$. The results obtained of cation conductivity measurements, providing a comparison between the cation conductivity without the apparatus 12 and measured after the cation exchange column ('On-line CEP CC'), with the apparatus 12 and measured between the apparatus 12 and the cation exchange column ('CC after the cell'), and with the apparatus 12 and measured after the cation exchange resin column ('CC after the cell—resin column configuration') are shown in FIG. 6. It can be seen that analogous cation conductivity values were obtained for the various measurements.

It was also found that 99,95% of the cations were removed by the apparatus 12, in terms of cation conductivity. The operating life of the resin column was extended by 3000%.

The Applicant believes that use of the apparatus 12 will substantially prolong the operational life of the resin in the column 16 before regeneration of the resin is required, thus ensuring production of ultra pure sample water for cation conductivity measurement, over long periods of time. Cation removal efficiency is promoted through use of the twin stage configuration of the apparatus 12. Additionally, the process is less labour intensive than without the apparatus 12 since less resin regeneration is required, and there is a saving in chemicals since less frequent regeneration is required. Less sample water is also required.

In FIGS. 7 to 10, reference numeral 100 generally indicates apparatus according to another embodiment of the invention, for treating water whose conductivity is to be measured.

Figure 7:
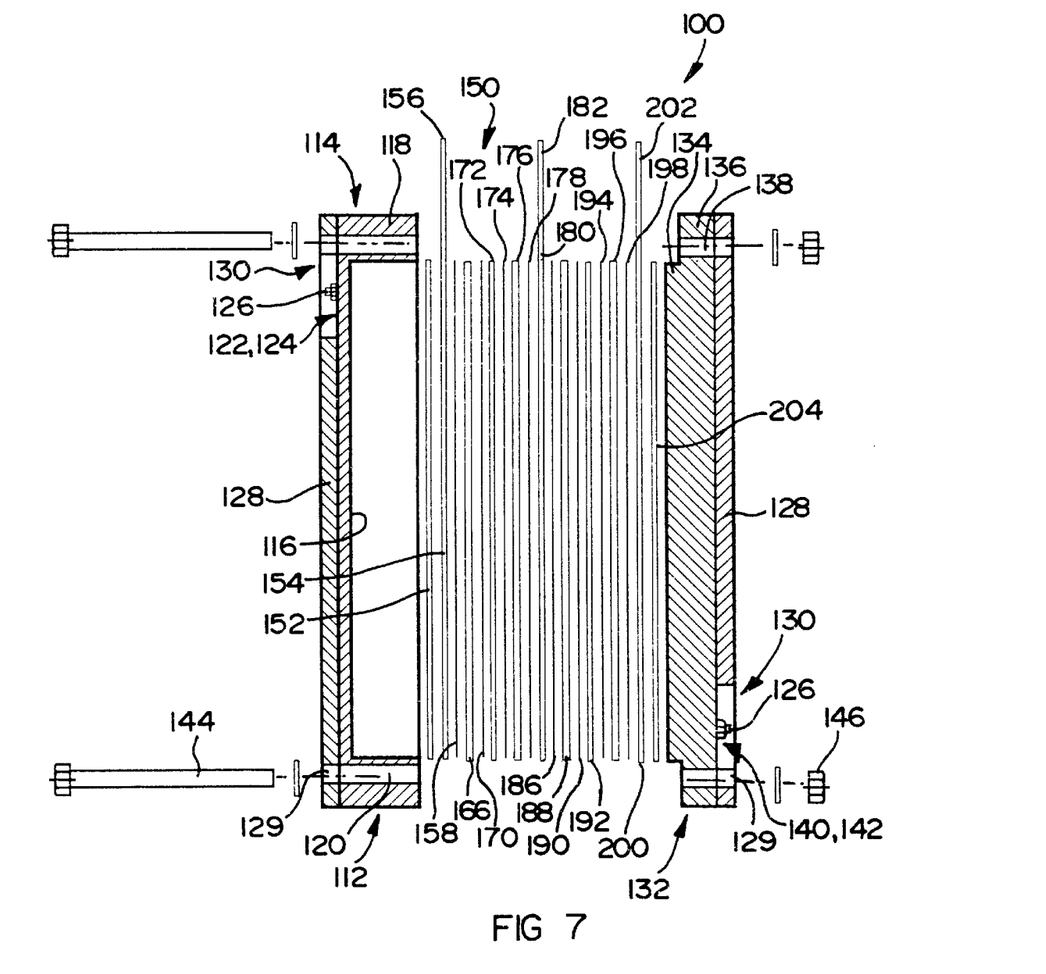
FIG. 7 shows an exploded sectional top view of an apparatus for treating water, according to the invention.
Figure 8:
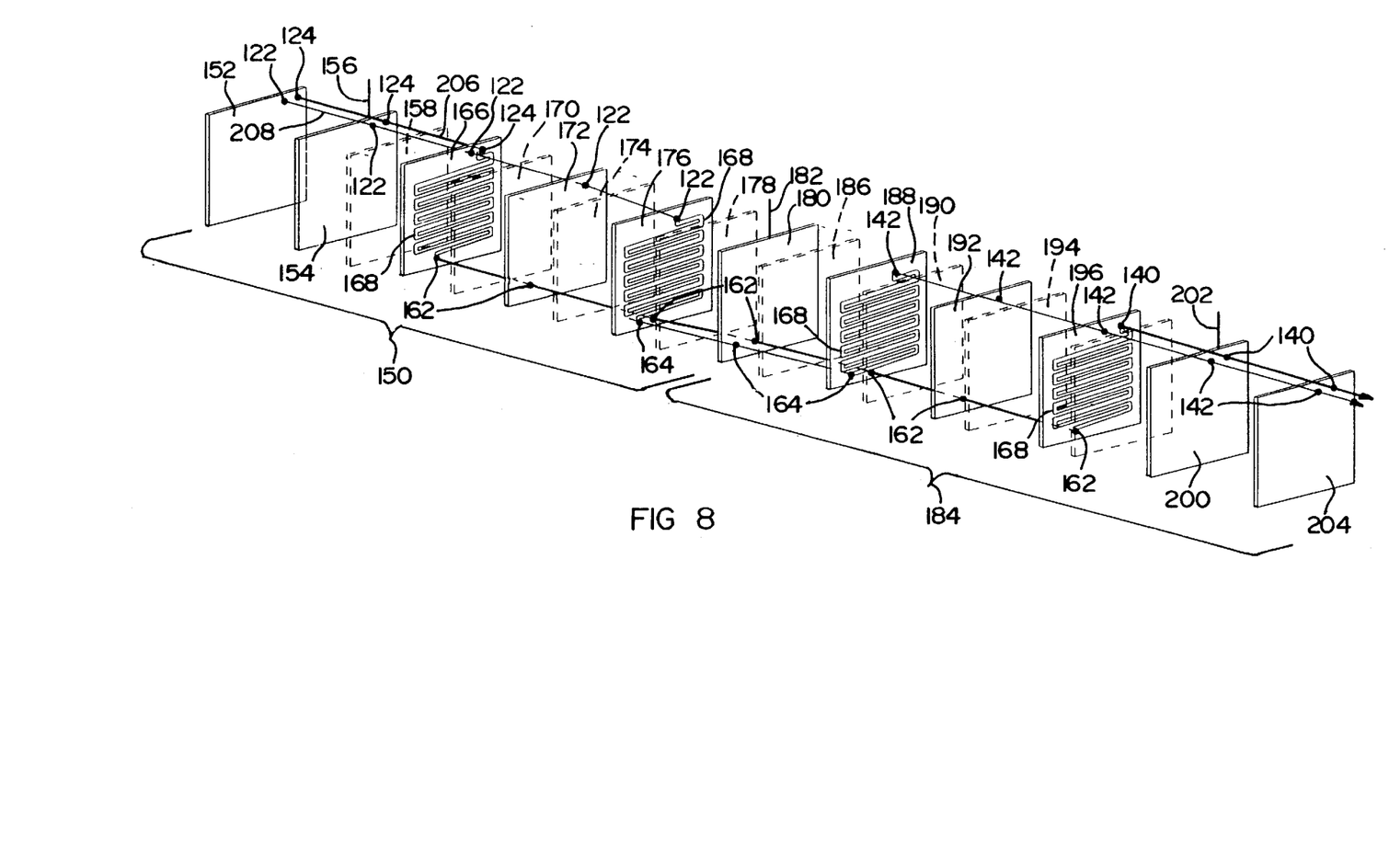
FIG. 8 shows an exploded view of part of the apparatus of FIG. 7.

The apparatus 100 includes a housing, generally indicated by reference numeral 112. The housing 112 comprises a female body component, generally indicated by reference numeral 114. The body component 114 comprises a base 116 which is almost square when seen from the front, e.g. typically being about 280 mm (upper and lower edge) by about 290 mm (side edges). A flange 118 protrudes from the base 116 and extends peripherally around the base 116. A plurality of bolt passageways 120, spaced peripherally apart, are provided in the flange 118. A pair of apertures 122, 124 are provided in the base 116, with these openings being fitted with threaded connectors 126. In the flange 118, along the upper side of the female body component 114 are provided openings (not shown) for receiving connectors of electrodes as hereinafter described. The female body component 114 is of electrically insulative material. Thus, it is typically of plastics material, such as polypropylene ('PP') or polyethylene ('PE').

A complementary backing plate 128 abuts the rear side of the female body component 114. The backing plate 128 has an aperture 130 which accommodates the connectors 126. The plate 128 is typically of stainless steel, anodized aluminium or powder coated mild steel.

The housing 112 also includes a male body component, generally indicated by reference numeral 132. The male body component 132 includes a central portion 134 which is receivable snugly within the flange 118 of the female body component 114, as well as a surround 136 which is complementary to the flange 118. Passageways 138, which are complementary to the passageways 120 in the flange 118 of the female body component 114, are provided in the surround 136. The male body component 132 is also of electrically insulative material, such as PP or PE. Passageways 140, 142 extend through the male body component 132. The openings or passageways 140, 142 are also provided with threaded connectors 126.

A backing plate 128 also abuts the rear surface of the male body component 132. The backing plates 128 are provided with apertures 129 which are complementary to the passageways 120, 138 so that the body components 114, 132 can be bolted together by bolts 144 extending through the apertures 129 and the passageways 120, 128, and nuts 146.

The apparatus 100 includes a first electrochemical cell stage, generally indicated by reference numeral 150, located within the housing 112.

The cell stage 150 includes a rubber gasket 152 which fits snugly within the flange 118 of the female body component 114, against the base 116 thereof. The gasket 152 has openings 122, 124 which are complementary to the openings 122, 124 in the base 116 of the female body component 114 and aligned therewith.

A positive electrode in the form of an anode plate 154 also fits snugly within the flange 118 of the female body component 114, and also has openings 122, 124 aligned with the openings 122, 124 in the base 116 and the gasket 152. The anode plate 154 is typically of stainless steel, nickel plated stainless steel or platinum coated nickel, and is about 0,9 mm thick. Stainless steel is used where a relatively low chemical stability is required, e.g. for high pressure boiler (17MPa operation) feed water, containing fairly low total dissolved solids. For lower pressure (8MPa or 12MPa operation) boiler applications, the more chemically resistant nickel plated stainless steel or platinum coated nickel would be used. An electrical connector 156 protrudes outwardly from the anode plate 154 through one of the openings in the upper side of the flange 118 of the female body component 114.

Figure 10:
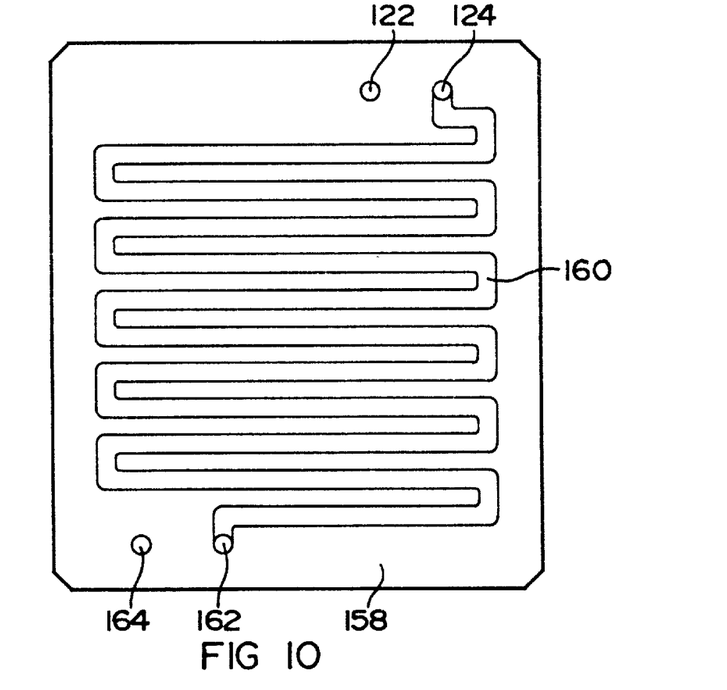
FIG. 10 shows a front view of one of the screens of the apparatus of FIG. 7.

A screen 158 abuts against the anode plate 154, and also fits snugly within the flange 118 of the female body component 114. The screen 158 is also of electrically insulative material, and is thus typically of plastics material. Thus, for example, it may be of polyethylene encapsulated in silicon rubber. The screen 158 has an opening 122 which is complementary to the opening 122 in the other components of the cell stage 150 and aligned therewith. A convoluted zig-zag shaped opening, channel or flow path 60 is provided in the screen 158, as shown in FIG. 10. The opening 160 extends through the screen 158 from its front surface. A fine mesh (not shown) spans the opening 160. Thus, the mesh is located between the front and rear faces of the screen 158. The opening 60 has, at one end thereof, a portion 124 which corresponds to the openings 124 in the other compartment and which is aligned therewith. At its other end, the opening has an end portion 162. An aperture 164, extending through the screen 158, is also provided in proximity to the opening 162. Typically, the opening or passageway 160 is about 8 mm wide.

Figure 9:
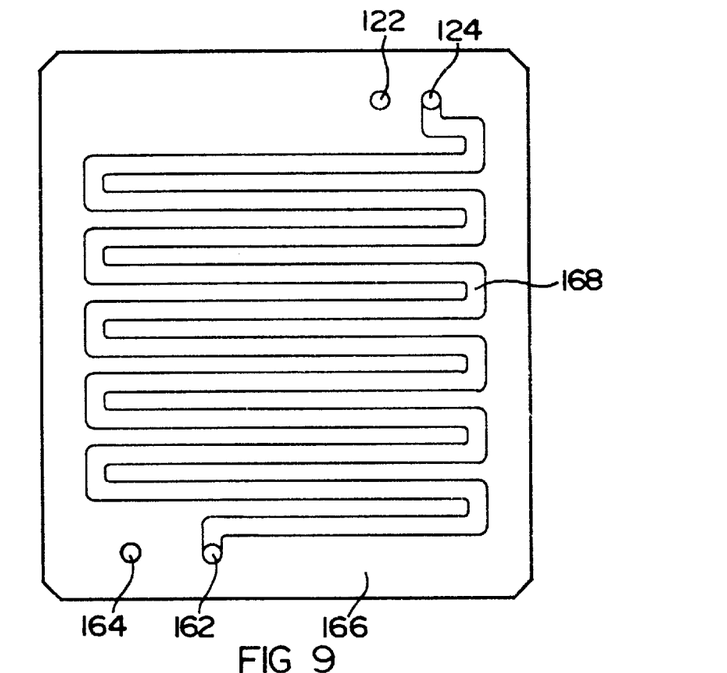
FIG. 9 shows a front view of one of the spacers of the apparatus of FIG. 7.

A spacer 166 abuts the screen 158, which is shown in more detail in FIG. 9. The spacer 166 is also provided with openings 122, 164 which are aligned with the openings 122, 164 in the other components. A convoluted zig-zag shaped opening, channel or flow path 168, which is complementary to the opening, channel or flow path 160 in the screen 158, is provided in the spacer 166. Thus, the opening 168 also has a start portion 124 which corresponds to the openings 124 in the other components and is aligned therewith, as well as an end portion 162 which is complementary to and aligned with the apertures 162 in the other components. The spacer 166 is typically of 3 mm thick polypropylene or polyethylene.

A screen 170 abuts the spacer 166. The screen 170 is substantially the same as the screen 158, with its convoluted opening or passageway matching the convoluted opening 168 in the spacer 166. Thus, the opening 160 of the screen 170 also extends from a start or inlet portion 124 to an end or outlet portion 162, which are aligned with the apertures 124, 162 respectively in the other components.

The anode plate 154, screen 158, spacer 166 and screen 170 together constitute an anode compartment of the electrochemical cell stage 150.

A water impermeable membrane 172 abuts the screen 170. The membrane 172 only has openings 122, 162 aligned with the openings 122, 162 of the other components. The membrane 172 is typically about 0,5 mm thick, and is capable of permitting passage of cations only.

A screen 174 abuts the membrane 172. The screen 174 is similar to the screens 158, 170, except that its convoluted opening has an inlet portion 122 aligned with the openings or apertures 122 in the other components, and an outlet portion 164, aligned with the openings or apertures 164 in the other components.

A spacer 176 abuts the screen 174, with the convoluted opening or passageway 168 of the spacer 176 being complementary to the convoluted opening or passageway of the screen 174.

A screen 178 abuts the spacer 176, and has a convoluted opening or passageway (not shown) which is complementary to and aligned with the opening or passageway 168 of the spacer 176.

The screens 174, 178 and the spacer 176 have complementary and aligned openings 162 which are aligned with the openings 162 in the other components.

A negative electrode in the form of a cathode plate 180 abuts the screen 178. It has openings 162, 164 aligned with the openings 162, 164 in the other components. The cathode plate 180 is also typically of stainless steel, nickel plated stainless steel, or platinum coated nickel, and is about 0,9 mm thick. An electrical connector 182 protrudes outwardly from the cathode plate 180 through one of the openings in the upper side of the flange 118 of the female body component 114.

The screen 174, spacer 176, screen 178 and cathode plate 180 together constitute a cathode compartment of the electrochemical cell stage 150.

The apparatus 100 includes a second electrochemical cell stage, generally indicated by reference numeral 184, also located within the housing 112. In other words, the cells 150, 184 are situated in parallel within the same or common housing 112.

The cell stage 184 includes the cathode plate 180. A screen 186 abuts the cathode plate 180. The screen 186 has a meshed opening 162 aligned with the opening 162 in the other components. It also has a convoluted meshed opening extending from an inlet portion 164, which is aligned with the opening 164 in the other components, to an outlet portion 122 which is aligned with the openings 122 in the other components of the cell stage 184.

A spacer 188 abuts the screen 186, and its convoluted opening 168 is complementary to and aligned with the convoluted meshed opening in the screen 186. The opening 168 thus has an inlet portion 164, and an outlet portion 142. It also has an opening 162 which is aligned with the opening 162 in the other components of the cell stage 184.

A Screen 190 abuts the spacer 188, and has a convoluted meshed opening which is complementary to and aligned with the convoluted opening 168 in the spacer 188. Its convoluted meshed opening thus also has an inlet portion 164 and an outlet portion 142. It also has an opening 162.

A membrane 192, which is similar to the membrane 172, abuts the screen 190. The membrane 192 has openings 142, 162 therein.

A screen 194 abuts the membrane 192, and is provided with an opening 142. The convoluted meshed opening of the screen 194 has an inlet portion 162 and an outlet portion 140 aligned with the openings 162 and the openings 140 respectively in the other components of the cell stage 184, and the housing 112.

A spacer 196 abuts the screen 194, and its convoluted opening 168 thus also has an inlet portion 162 and an outlet portion 140. It also has an opening 142.

A screen 198 abuts the spacer 196, and is complementary to the screen 194.

A positive electrode in the form of an anode plate 200 abuts the screen 198 and is provided with apertures 142, 140. An electrical connector 202 protrudes outwardly from the anode plate 200 through one of the openings in the upper side of the flange 118 of the female body component 114.

A rubber gasket 204, having openings 142, 140, abuts the anode plate 200.

The cathode plate 180, screen 186, spacer 188 and screen 190 constitute a cathode compartment of the cell 184, while the screen 194, spacer 196, screen 198, and cathode plate 200 constitute an anode compartment of the cell stage 184.

In use, sample water from a steam/water circuit of a power station and containing $NH_4OH$ enters the apparatus 100 and passes sequentially through the anode compartments thereof, as indicated by the flow path 206. At the same time, demineralized water passes sequentially through the cathode compartments in cocurrent fashion, as indicated by the flow path 208. A DC current is passed between the anode plate 154 and the cathode plate 180, as well as between the anode plate 200 and the cathode plate 180. Reactions (1) to (6) as hereinbefore described take place, thereby removing cations of inorganic salts from the sample water, and replacing them with hydrogen ions to produce acids of the inorganic salts, as hereinbefore described. This will remove most of the cations of dissolved salts present in the sample water. The sample water exiting from the apparatus 100 can be subjected to cation conductivity measurement in a suitable cell. If necessary, a strong acid cation exchange resin column (not shown) can be located between the apparatus 100 and the conductivity measurement cell.

The openings or passageways 160, 168 thus provide turbulent tortuous water flow paths in the anode and cathode compartments. Such turbulence allows a higher electrical current to flow per unit area and, in respect of the sample water, aids in keeping the sample water intimately mixed which promotes transfer of ions to the surface of the membrane.

The membranes 172, 192 may also be those available in South Africa under the trade name IONICS. Thus, the membranes have negative charges affixed to sites throughout the membranes. These fixed negative charges repel negatively charged ions or anions while allowing cations to permeate through the membranes.

If desired, further electrochemical cell stages (not shown) can be provided in the same housing 112, adjacent to the anode plate 200, so that the anode plate 200 is then a common electrode for the cell stage 184, and the further cell stage. The further cell stage will then also comprise, sequentially, a screen against the anode plate 200, a spacer, a screen, a membrane, a screen, a spacer, a screen, and a cathode plate.

The cell in which the conductivity measurement takes place can, as hereinbefore described, be a single conductivity/resistivity transmitter such as Model Polymetron Monec C8920 of Zellweger Uster AG of Switzerland.

The Applicant believes that, with the apparatus 100, cation removal from sample water prior to cation conductivity measurements, can be sustained over long periods of time. If desired, a resin column can be located downstream of the apparatus 100, but the Applicant believes that the apparatus 100 can produce sufficiently pure water on its own for subsequent cation conductivity measurement. Cation removal efficiency is promoted through the use of the multistage configuration of the apparatus 10 wherein the cell stages are located within the same cavity of the housing and wherein a common cathode plate is used for two cell stages.

We claim:

1. Apparatus for treating water, which apparatus comprises a housing;

a first electrochemical cell stage in the housing, the first cell stage having a first anode compartment and a first cathode compartment with a first sample water inlet leading into the first anode compartment and a first sample water outlet leading from the first anode compartment and with a first demineralized water inlet/outlet leading into/from the first cathode compartment and a second demineralized water inlet/outlet leading into/from the first cathode compartment;

a second electrochemical cell stage in the housing, the second cell stage having a second anode compartment and a second cathode compartment with a second sample water inlet leading into the second anode compartment and being connected to the first sample water outlet of the first cell stage and a second sample water outlet leading from the second cathode compartment, with a third demineralized water inlet/outlet leading into/from the second cathode compartment and being connected to the second demineralized water inlet/outlet of the first cell stage, and a fourth demineralized water inlet/outlet leading into/from the second cathode compartment;

an electrode associated with each of the compartments; and a water impermeable membrane capable of transferring only cations, for each of the cell stages, the membrane in each cell stage separating its anode compartment from its cathode compartment.

2. Apparatus according to claim 1, wherein the cell stages are such that either the first and second anode compartments or the first and second cathode compartments are arranged back-to-back, with a common electrode provided for the back-to-back compartments while a separate electrode is provided in each of the other compartments.

3. Apparatus according to claim 1, wherein the inlets and outlets are arranged such that the direction of flow of the sample water and demineralized water through the compartments, in use, is in cocurrent fashion.

4. Apparatus according to claim 1, which includes at least one further electrochemical cell in the same housing, the further cell also having an anode compartment, a cathode compartment, water inlets and outlets, at least one electrode, and a water impermeable membrane, with the further cell arranged such that sample water and demineralized water can flow sequentially from the first or second cell through the further cell.

5. A water cation conductivity measurement installation, which comprises apparatus according to claim 1, for treating water whose cation conductivity is to be measured;

optionally, a strong acid cation exchange resin column operatively connected to the sample water outlet of the apparatus; and a conductivity-measuring cell operatively connected to the apparatus or to the column so that sample water can pass from the apparatus or the column to the cell.

* * * * *